United States Patent [19]
Frechet et al.

[11] Patent Number: 5,968,097
[45] Date of Patent: Oct. 19, 1999

[54] ELASTIC DEVICE FOR EXTENDING LIVING TISSUE AND HAVING LARGE CAPACITY FOR ELONGATION

[75] Inventors: Patrick Frechet, Paris; Guy Charvin, Antibes, both of France

[73] Assignee: MXM, Antibes, France

[21] Appl. No.: 08/995,488

[22] Filed: Dec. 22, 1997

[30] Foreign Application Priority Data

Dec. 20, 1996 [FR] France .................................. 96 16078

[51] Int. Cl.⁶ ...................................................... A61F 2/10
[52] U.S. Cl. ........................... 623/15; 606/213; 606/215; 606/187
[58] Field of Search .............................. 623/15; 606/187, 606/213, 215–221, 225

[56] References Cited

U.S. PATENT DOCUMENTS

| | | |
|---|---|---|
| 679,993 | 8/1901 | Ross . |
| 2,012,755 | 8/1935 | De Muth . |
| 2,421,193 | 5/1947 | Gardner . |
| 2,472,009 | 5/1949 | Gardner . |
| 2,575,205 | 11/1951 | Brown . |
| 2,619,084 | 5/1952 | Brown . |
| 2,669,747 | 2/1954 | Detaranto . |
| 3,068,869 | 12/1962 | Shelden et al. . |
| 3,473,528 | 10/1969 | Mishkin et al. . |
| 4,007,743 | 2/1977 | Blake . |
| 4,073,298 | 2/1978 | Le Roy .................................. 606/216 |
| 4,430,998 | 2/1984 | Harvey et al. .......................... 606/216 |
| 4,535,772 | 8/1985 | Sheehan . |
| 4,676,245 | 6/1987 | Fukuda . |
| 4,865,026 | 9/1989 | Barrett . |
| 4,955,395 | 9/1990 | Manders . |
| 4,976,726 | 12/1990 | Haverstock . |
| 4,994,073 | 2/1991 | Green . |
| 5,234,462 | 8/1993 | Pavletic .................................. 606/215 |
| 5,263,971 | 11/1993 | Hirshowitz . |
| 5,441,540 | 8/1995 | Kim ....................................... 606/216 |
| 5,486,196 | 1/1996 | Hirshowitz et al. . |
| 5,507,775 | 4/1996 | Ger et al. . |
| 5,531,760 | 7/1996 | Alwafaie . |
| 5,531,790 | 7/1996 | Frechet et al. . |
| 5,549,713 | 8/1996 | Kim . |
| 5,556,428 | 9/1996 | Shah . |
| 5,618,310 | 4/1997 | Ger et al. . |
| 5,662,714 | 9/1997 | Charvin et al. .......................... 623/15 |
| 5,665,108 | 9/1997 | Galindo .................................. 606/215 |
| 5,723,009 | 3/1998 | Frechet et al. .......................... 623/15 |

FOREIGN PATENT DOCUMENTS

| | | |
|---|---|---|
| 0279534 | 8/1988 | European Pat. Off. . |
| 0432743 | 6/1991 | European Pat. Off. . |
| 0418970 | 12/1910 | France . |
| 0854340 | 4/1940 | France .................................. 606/215 |
| 2715292 | 7/1995 | France . |
| 9601824 | 10/1996 | France . |
| 1412751 | 7/1988 | U.S.S.R. . |
| 9300441 | 8/1993 | WIPO . |
| 9321849 | 11/1993 | WIPO . |

OTHER PUBLICATIONS

Scalp Extension from Patrick Frechet, Dermatol Surg Oncol Magazine (1996).
"Hair Transplantation" (pp. 504 to 518).
"Scalp Flexibility", Dr. Richard C. Shiell, 1992.
Advertising for "Koken".
"Focus", *Facial Plastic Surgery Today*, Third Quarter, 1990.

*Primary Examiner*—Mickey Yu
*Assistant Examiner*—Bruce Snow
*Attorney, Agent, or Firm*—Dvorak & Orum

[57] ABSTRACT

A device for extending living tissue includes at least two rigid supports that respectively have a plurality of hook-like barbs on one end thereof for attachment to the skin, each point of attachment corresponding to a respective edge of the areas of tissue to be treated, while the other end of each support includes at least one guide for receiving a flexible extendable elastic belt therearound, the belt having a portion extending parallel along at least one of the rigid supports.

9 Claims, 3 Drawing Sheets

ELASTIC DEVICE FOR EXTENDING LIVING TISSUE AND HAVING LARGE CAPACITY FOR ELONGATION

The present invention relates to a novel elastic device of large elongation capacity for extending living tissue, and since it is used in the same surgical method, with the same basic technique, and acts on the same principles, it comes in the same family as the devices described in earlier PCT patent application No. WO 93/21849 filed by the same proprietors as the present application and published on Nov. 11, 1993. Certain references thereof are either repeated in full in the present application, or are merely mentioned so as to enable the person skilled in the art to refer thereto.

FIELD OF THE INVENTION

The technical field of the invention is the field of making surgical materials suitable for implanting in the human body.

BACKGROUND OF THE INVENTION

As in the above-mentioned earlier patent application, one of the main applications of the present invention lies in making implantable extender devices to operate for a determined length of time beneath the scalp in order to diminish baldness, however other applications can be envisaged for the device of the invention, whenever it is useful or necessary to stretch tissue, for example to diminish wounds, or scars, or tattoos, or pigmented naevi; it is sometimes necessary to cover the surface concerned with new skin, particularly when the previous skin has been destroyed or damaged by burning, tumors, injury, etc.

Concerning baldness, known medically as "male-pattern alopecia", which is definitive and applies to one in three of men aged 50, the only effective therapy is surgical, as follows: a portion of the healthy follicles that are genetically programmed to last throughout life is surgically redistributed, which in practice means taking hair from around the tonsure.

Various methods of intervention and specific devices are known at present, such as those described in the earlier patent application: they can be characterized by three basic techniques, namely: implants, reductions of the tonsure, and flaps. All of them consist in moving hair-carrying scalp to take the place of some or all of the bald scalp. The present invention relates to the second of those techniques, and a method of intervention is described using devices that are specifically claimed in the above-mentioned patent application No. WO 93/21849 and then in FR No. 2 715 292, having the same Applicants, so there is no need to reproduce the general introduction and detailed description thereof in the present application.

It is merely recalled that there exist at present three methods of intervention, all using the same technique of reducing the tonsure and each of them making use of specific devices. The most recent method is that developed and tested successfully since filing the above-mentioned first patent application: it describes and teaches extender devices for that purpose in particular. Such a device comprises both elastic means of outside dimensions in an active extended position such that a portion of its perimeter corresponds substantially with and underlies the edges of at least a portion of the area of tissue to be treated, and at least two hooking means, each secured to one end of the elastic means, the ends being opposite each other in the active elastic direction of said elastic means, and enabling the device to be fixed in said tissue along said edges.

The present invention relates to a novel type of elastic extender device that operates on the same principle and that is used with the same intervention method: such devices are also called "extenders" since they act by selectively stretching surface area. It can thus be recalled that by using such devices with the method in question, good results are obtained in reducing tonsure, with few surgical interventions, and throughout the duration of treatment the appearance of the head remains sufficiently acceptable to enable the person concerned to continue with any normal activity, and no follicles are destroyed by ischemia of the surface layers of the scalp unlike that which has been observed in other techniques. When extender devices are applied, advantage is taken of the ability of living tissue, such as the scalp, to be stretched in the same manner as has been performed with balloons (which constitute one of the other two above-mentioned prior art methods of intervention for reducing tonsure). However, in the present case there is a great advantage associated with the fact that the tissue or hair-carrying scalp is stretched and distorted progressively but without any increase in volume. Thus instead of the total area increasing in the same manner in all directions, area is increased in predetermined directions only. There is thus firstly no change in morphology, and in particular in the shape of the head when the scalp is involved, and secondly there is no stretching in directions that are not useful.

Also, since the active ends of the extender device can be placed exactly at the edges of the zones or areas of tissue to be treated that are to be subjected to traction in order to change area, zones that are not to be stretched are not subjected directly to said tension: thus, when stretching the scalp, there is no secondary stretching of the bald zones, thereby improving the effectiveness of the system and the speed of its action.

Nevertheless, at present with known extender systems such as those described in the above-mentioned patents, and when it is desirable to have an extender of fairly large elongation capacity in order to be able to anchor its hooking means far apart (depending on the dimensions of the area of the bald zone to be reduced), it becomes necessary to increase the length of the elastic means interconnecting the hooking systems when at rest. If the device has a large elongation coefficient, e.g. such as 200% or 300%, there will always remain between the hooking systems a rest length of the elastic means equal to L for a maximum amount of dynamic variation in stretching by the hooking systems respectively equal to 2L or 3L.

OBJECTS AND SUMMARY OF THE INVENTION

As in the above-mentioned earlier invention, the problem posed is thus firstly to be able to increase a given area of living tissue by a determined amount by elongation due to the reproductive facility of its cells, while limiting secondary stretching of zones that need not be involved, and to do so with a minimum number of interventions and over a duration that is as short as possible, and secondly to be able, at rest, to bring the supports of the hooking systems as close together as possible while still having elongation capacity of the elastic means between said supports greater than the capacity that is given solely by the elongation coefficient of the elastic means, and while conserving sufficient return traction force between the supports of the hooking systems.

Another problem associated with the above is that of being able to move together to any desired extent, even to practically touching, the edges of the areas of tissue concerned, with at least one of the areas being elongated, and to be able to do this as simply as possible, with overall elongation of the entire area of tissue concerned being homogeneous, without any unsightly deformation of the volume of the part of the body covered by said tissue; as obtained in the second above-mentioned patent FR No. 2 715 292 which teaches at least two independent elastic means, each fixed at at least one of its ends to at least one of the hooking means of the type described in the first earlier PCT application No. WO 93/21849, and at least one substantially rigid and non-moving support which is connected to at least one of the elastic means which deforms and moves relative to said support against which the elastic means entrain said hooking means closer thereto and thus entrain the edges of the area of living tissue that is to be treated: that solution is indeed satisfactory, but the present invention proposes a novel and other solution.

The main object of the present invention is achieved by an elastic device for extending living tissue comprising in a manner known from the documents cited in the introduction, at least one flexible elastic means, interconnecting at least two hooking means each secured to a rigid support and such that in an active position in which the elastic device has been elongated by traction in at least one given direction XX', said hooking means correspond at least to the edges of the areas of tissue to be treated; according to the present invention, said flexible elastic means is constituted by a belt of flexible material that is deformable and extensible, having a portion thereof mounted along at least one of said rigid supports for the hooking means and slidable through at least one guide means fixed to the same rigid support: this belt portion then constitutes a reserve of elastic energy enabling the device to be extended further than in known devices.

In a particular embodiment, said belt of elastic flexible material is an endless belt and it slides through at least two guide means fixed to each rigid support, said belt having as many portions disposed along one of said rigid supports and as many portions interconnecting them as there are rigid supports.

In particular, in an embodiment, the elastic device for extending living tissue includes at least three rigid supports for hooking means, constituting a polygon which, in a rest position, has as many sides as it has rigid supports, and in an active, extension position has twice as many sides.

In another embodiment, said device has only two rigid supports, thus constituting the novel solution mentioned above capable of bringing together the edges of the areas of tissue concerned by any desired amount, and even so that they are practically one against the other.

At present, using prior devices that likewise include two rigid supports, it is necessary to pull on hair-carrying zones that are set back from the boundary of the bald zone, so that at the end of extension, when the extender has returned to its rest position, its ends remain a certain distance apart, which distance corresponds to the width of the hair-carrying margins situated and held between the ends of the device. Those prior extender devices do not enable their hooking systems anchored in the galea of the scalp to be moved close enough together because, even in the rest position, some length of elastic means subsists between the hooking systems, as explained above; this makes it necessary:

Either, as mentioned above, to pull on the hair-carrying scalp from zones of tissue situated behind the actual boundary of the bald zone, so as to leave a margin of hair-carrying scalp between the hooking systems, however that gives rise to unequal distribution of hair between zones that have been stretched because they are situated beyond the hooking systems and the zones that have not been stretched because they are situated between the hooking systems;

Or else to perform several interventions in succession and to finish off moving the edges of the hair-carrying zones by an intervention of the third type of the previous methods mentioned in the introduction, namely bringing the edges together under direct tension from surgical sutures, with the drawback that that can give rise to a scar that is rather visible. Clearly, when using a device of the present invention that has more than two hooking systems, thereby forming a polygon, there will remain a central area between the rigid supports even when they are at rest, nevertheless that area is already reduced more than it would be using the elastic means of previously known devices, and secondly it can be diminished by a single further intervention, e.g. using another device of the invention having only two hooking supports.

In a preferred embodiment, the elastic device of the invention includes a slide plate of area not less than that of the device when in its elongated, active position, which plate is disposed against the elastic means and beneath them relative to the hooking means.

The object of the invention can then be achieved with the above device, as described by way of example in the accompanying figures, and by applying the following steps:

Such an elastic device is used which, in the rest position has only two rigid supports which are therefore substantially touching, covering only a small area and thus capable of being slid easily into an incision within and beneath the living tissue to be treated;

The device is elongated by applying traction to the rigid supports moving them away from each other, and the hooking systems are moved apart by an amount that corresponds to the edges of the tissues to be treated;

For this purpose, the living tissue that is to be treated is separated and detached from the underlying tissue and said hooking systems are anchored therein along the edges of the areas of tissue that are to be treated; and The incision used for installation is then closed, and said hooking supports are then urged back towards each other by the tension from the elastic means, and if so desired this can continue until they come into contact, with this being made possible by the reserve of elastic energy and of length that is made available by those portions of belt that are mounted along or parallel to said rigid supports.

The result is novel devices for extending living tissue using the same technique and the same method as the extender devices described in the earlier application mentioned in the introduction, but having novel and specific characteristics. These devices make it possible to satisfy the problem posed and to eliminate any drawback that may be identified in known devices: in particular, the elastic portions that are mounted along and thus practically parallel to the rigid supports have the effect of giving the device a considerable reserve of elastic energy, while also allowing the rigid supports to come into contact with each other in the rest position; in this way, with an elastic material constituting the belts that has an elongation coefficient of 200% or 300%, for example, and even as much as 500%, it is possible to move the hooking supports apart from zero separation to a distance that is equal to two, three, or five times, respectively, the width of said supports, providing the belt portions mounted parallel thereto have the same length as the supports.

Further, when the device has only two hooking supports, it is possible to bring together the edges of the tissue concerned, such as the scalp, by any desired amount, and in the limit they can even be very close to each other; as mentioned above, it is possible to bring the edges of the bald zone practically together by pulling on all of the hair-carrying zones in uniform manner without any need to leave portions thereof between the hooking systems, thus avoiding any need for secondary intervention. By using the devices of the present invention, a single intervention can suffice, and because the edges of the tissue on which the stretching has been performed can be moved together by any desired amount and can be practically touching, the scar where said edges join can be reduced to a minimum, thereby leaving an unsightly mark that is as small as possible.

Also, the sliding system placed between the elastic means and the subcutaneous tissue, since it is stationary relative thereto and since it isolates it from the elastic means, spares the subcutaneous tissue from any rubbing or harm therefrom: this improves effectiveness and eliminates any interfering effect that could impede the desired amount of extension.

It may also be observed that it is possible to reduce the duration of treatment further than when using previous devices known from the patent application cited in the introduction: the overall cost of treatment is decreased, and so is the pain to which the person concerned is subjected. This is particularly satisfactory in that the bald area removed is much larger than with any previously known method or device.

Other advantages of the present invention could also be mentioned, but those mentioned above already suffice to demonstrate the novelty and the advantage thereof.

BRIEF DESCRIPTION OF THE DRAWINGS

The following description and figures relate to embodiments of the invention, but they are not limiting in any way: other embodiments are possible within the scope and the extent of the present invention, in particular by changing the shape and the type of the elastic means, and also the shape and the type of the hooking means and of the rigid supports. It may be observed that the following description and figures, and the explanations below, relate essentially to the main application of the invention to reducing baldness, however it is clear that all of the devices of the present invention can be used in other types of application that require or seek tissue to be stretched, such as, in particular, making skin firmer or re-covering zones that have been destroyed or damaged, as mentioned in the introduction.

MORE DETAILED DESCRIPTION

Figure 1:
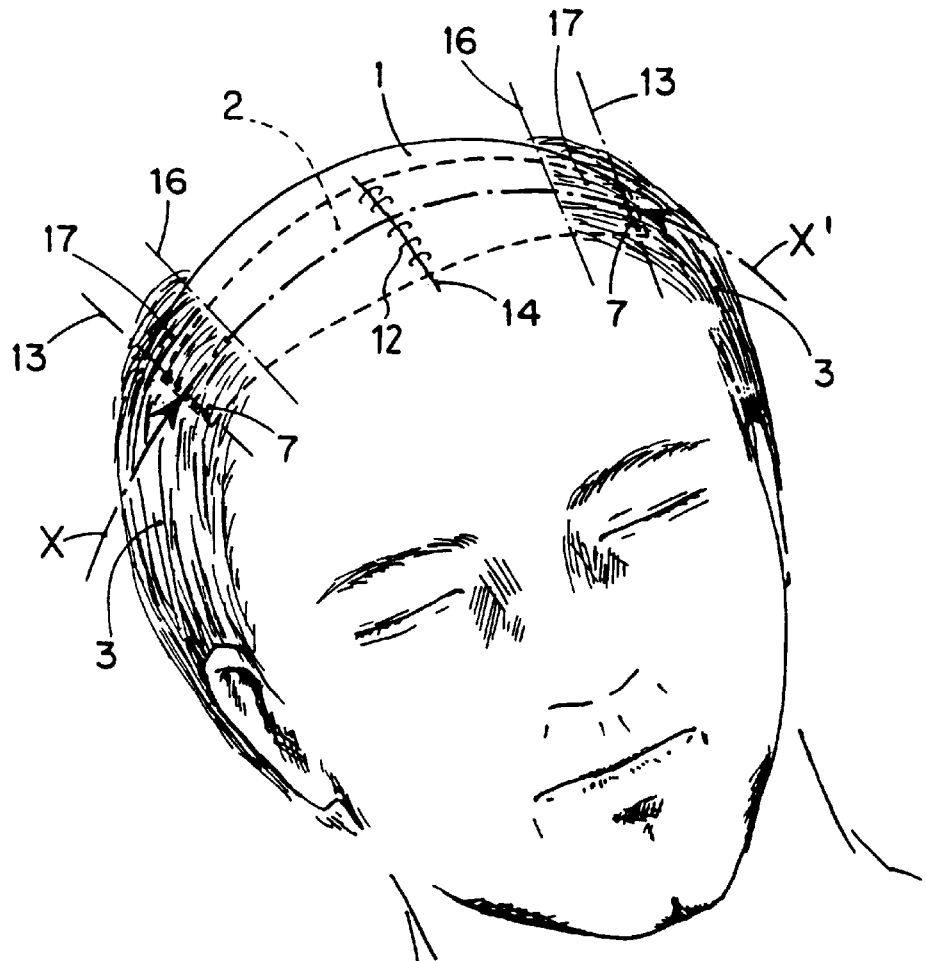
FIG. 1 is a diagrammatic perspective view of the device of the invention including two rigid supports and implanted on the skull of a partially bald person.

FIG. 1 is a diagrammatic perspective view of the head of a person whose scalp includes a bald zone 1 and hair-carrying zones 3 situated at the periphery of the bald zone 1.

Figure 2:
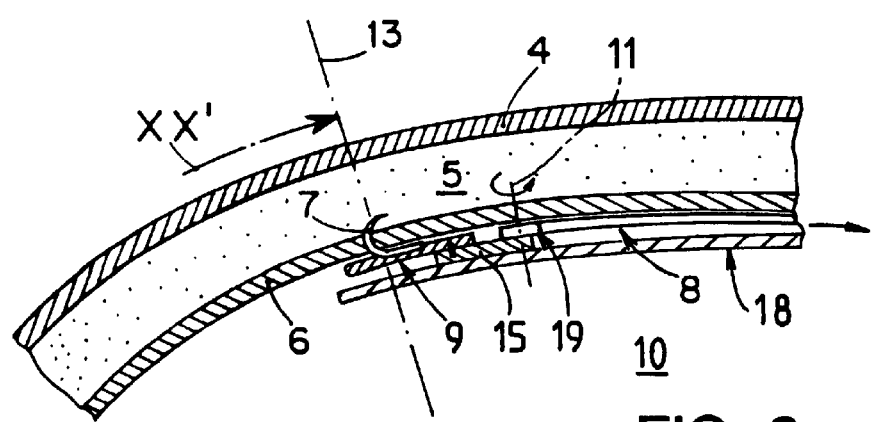
FIG. 2 is a fragmentary section view of the hooking of the device beneath the scalp of the person.
Figure 3:
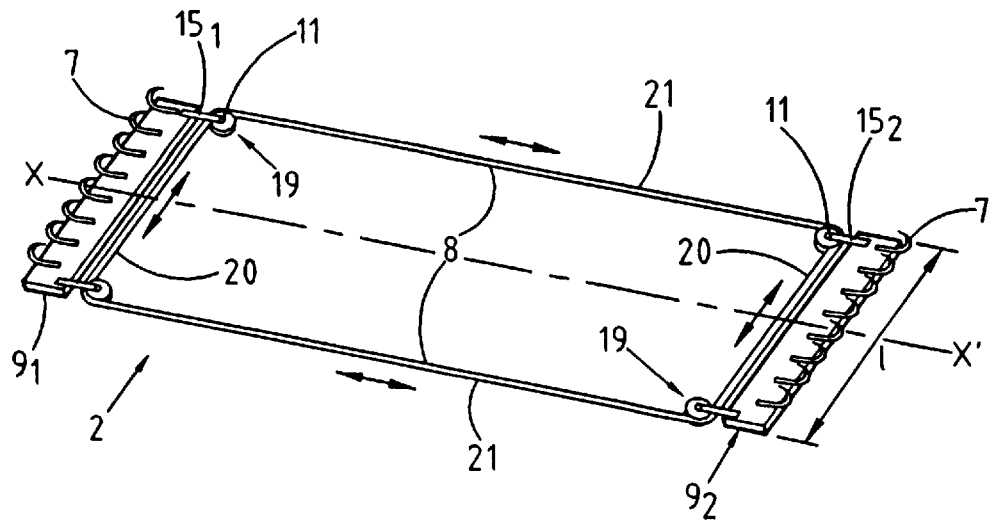
FIG. 3 is a perspective view of a device of the kind shown in FIG. 1 in its extended position.
Figure 4:
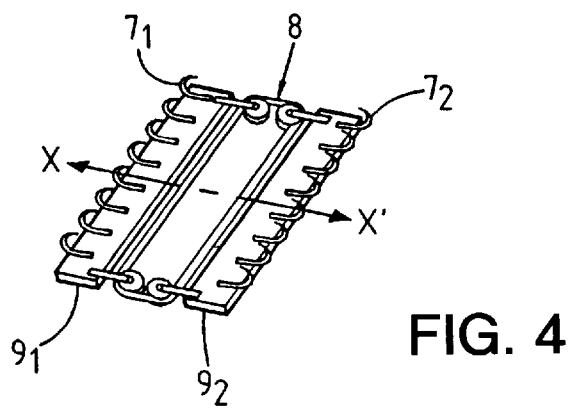
FIG. 4 is a perspective view of the FIG. 3 device in its rest position.
Figure 5:
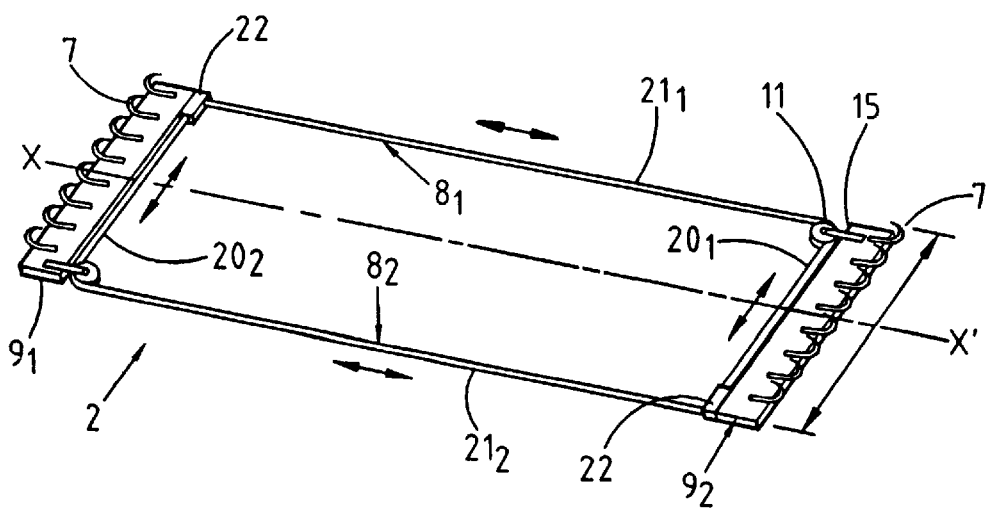
FIG. 5 is a view of another type of device of the invention having two rigid hooking supports in the extended position.

The extender device 2 of the present invention is placed beneath the scalp by making an incision 14 in the middle of said bald zone 1:

the hooking systems 7 (each of which is secured to a rigid support 9 that is connected to at least one elastic means 8) are spaced apart to correspond to the edges 13 of the tissue to be treated by applying traction to extend said flexible elastic means 8 interconnecting them; such a device is represented in FIG. 1 in the form of a dashed-line rectangle, with the device in question using two hooking systems as shown in FIGS. 3 to 5;

said tissue 5 to be treated is separated and detached from the underlying internal subcutaneous tissue 10 and said rigid supports 9 of said hooking means 7 are placed beneath the separated tissue 5; and As shown in section in FIG. 2, said hooking means 7 (which may be constituted by hooks, for example) are then anchored in the galea and the hypoderm (which is the rigid fibrous layer constituting the deep portion of the scalp).

Thus, throughout the stage during which the elastic means 8 are contracting and therefore extending the areas 3 of living tissue beyond the hooking systems 7 of the device 2 in an extension direction XX' which, for a system having two rigid hooking supports, is the direction in which the longitudinal portion(s) 21 of said elastic means 8 are stretched, a portion 20 of the driving element of the elastic means 8 remains along, if not parallel to, the hooking means 7, i.e. it remains substantially perpendicular to the direction XX'.

Said hooking systems 7, which can thus be hooks or any other gripping system that adheres to tissue, such as pins passing through the structure to be stretched or loop pins of the safety pin type, are thus put into place along the edges 13 of at least a portion of the area of tissue 5 to be treated, which in this example is the scalp for the purpose of moving towards each other hair-carrying zones 3; these edges 13 are not necessarily the boundaries 16 between hair-carrying zones 3 and the bald zone 1; however with the present invention and using systems having two rigid hooking supports 9, that becomes possible in practice since, as mentioned above, at the end of tissue stretching when the extender 2 has returned to its rest position as shown in FIG. 4, the hooking systems 7 can be situated almost against each other, and there is therefore no need for large hair-carrying margin zones 17 to be located between the hooking systems when the device is initially installed: in this way, the boundaries 16 between the hair-carrying zones and the bald zone 1 can practically coincide with the edges 13 of the zones to which the hooking systems 7 are hooked so as to ensure that the hair-carrying zones 3 are stretched in their entirety.

As in the earlier patent application mentioned in the introduction, it is not necessarily useful or appropriate to act in uniform and continuous manner along the entire length of the edges 13 of the area to be treated; it is possible to pull on and hook to only a portion thereof or non-adjacent zones thereof, depending on the state of the tissue and the result that is to be obtained, e.g. by using extender device shapes that do not necessarily include hooking systems disposed in continuous straight lines, as shown in the accompanying figures: they may be curved, discontinuous, etc. . . . , as known at present from the document cited in the introduction; adjacent zones lying between two points or two lines of traction will be entrained indirectly to a greater or lesser extent depending on how the hooking systems 7 are disposed, and thus even when pulling only on a portion of the edges 3 of the zone to be treated, all of the zone will be subjected to extension, however this will be done in a manner that is selective, determined, and defined, thereby making it possible to obtain the best desired result.

Figure 6:
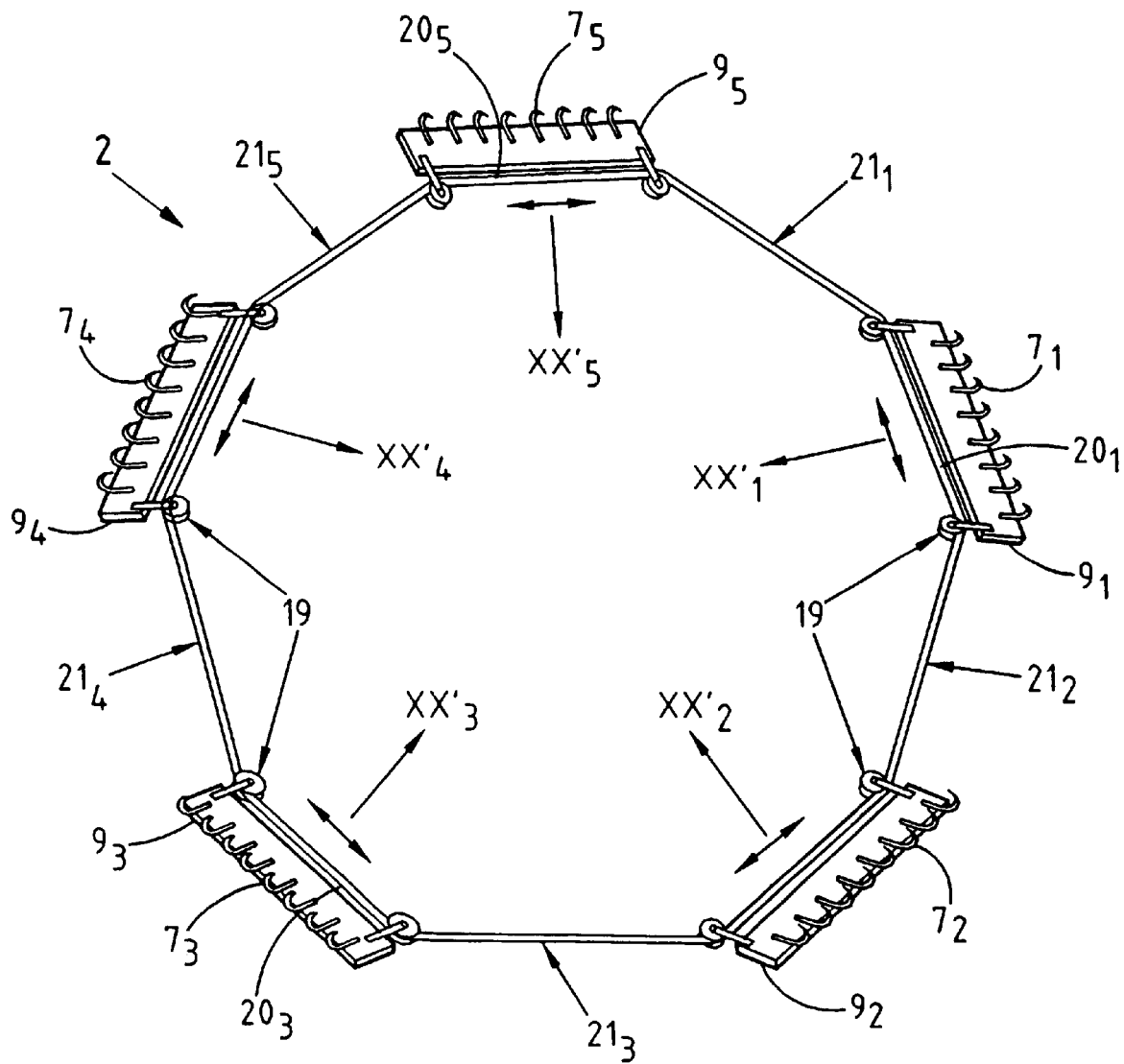
FIG. 6 is a perspective view of a device of the invention in a semi-extended position and comprising five rigid hooking supports forming a pentagon in the rest position and a decagon in the extended position.

The same applies to using a device having a plurality of rigid hooking supports 9, as shown in FIG. 6: in such a system, as indeed in those shown in FIGS. 3 to 5, the respective lengths of the rigid supports can be different and the anchoring provided by the hooking systems 7 can be performed asymmetrically relative to the center of the polygon formed by the rigid supports when in the rest position, e.g. for the purpose of compensating for possible lack of symmetry in the bald zone relative to the adjacent hair-carrying zones; the traction force on each rigid support 9 is then the resultant of the tension forces transmitted by the two portions 21 of the elastic means 8 adjacent to the rigid support 9 in question and connecting it to two adjacent rigid supports, and so on for the others, defining respective extension directions $XX'_1$ for each of said rigid supports $9_1$.

In the example of FIG. 1, the extension device or "extender" e.g. implemented as shown in FIGS. 3 and 4, is put into tension while it is being installed, e.g. using tools of the kind mentioned and described in the earlier patent application cited in the introduction. The elastic means 8 as described below will subsequently contract progressively and pull the tissue 5 in the hair-carrying zones 3 in its actively elastic direction XX' as originally stressed and will return to its initial length, moving the hooking systems 7 towards each other; the systems will thus move towards each other together with said edges 3, thus compressing the bald zone 1 situated between them, until said edges 3 are practically united if that is so desired, or until they have reached a desired separation distance if that was predetermined; the length of the elastic means 8 can be calculated to conserve a certain desired distance at rest between the edges 13 depending on the type of application and on the desired result, as with the devices of the earlier patent. Confidential experiments have shown that this extension followed by total compression when the edges 13 are to be completely united, can be achieved over a period of about one month, particularly when the edges 13 practically coincide with the boundaries 16 of the hair-carrying zones.

The scar 14 which enables the said device 2 to be installed can then be reopened to enable the device to be removed and to cut off the bald strip 1 which is then naturally in excess, and the boundaries 16 can be sewn together directly, by any conventional closure means 12 for closing the opening 14. The desired effect is thus obtained, i.e. the hair-carrying zones have been stretched uniformly and no further intervention is necessary.

FIG. 2 is a section view through the scalp in which the device of the invention has been anchored via one of its hooking systems 7 penetrating into the galea and the hypoderm 6 which is the fibrous surface situated beneath the scalp 5 proper, which is itself protected by the outer skin 4: in FIG. 2, the device shown is that of FIG. 3 or 4, for example, and comprises a slide plate 18 of area not less than that of the device 2 when in the active extended position, and disposed against and beneath the elastic means 8 relative to the hooking means 7, thus separating the device 2 from the internal subcutaneous tissue 10.

In the embodiments shown in FIGS. 3 to 5, the extension devices 2 for extending living tissue such as the scalp mentioned as an example of a main application in FIGS. 1 and 2, comprise in conventional manner, at least one flexible elastic means 8 interconnecting at least two hooking means 7, each of which is secured to a rigid support 9, and such that in an active position in which the device 2 is elastically extended by applying traction in a given direction XX', said hooking means 7 correspond at least to the edges 13 of the areas 3 of tissue to be treated.

In the present invention, said flexible elastic means 8 is constituted by a belt of flexible material that is deformable and stretchable, having a portion 20 thereof mounted along at least one of said rigid supports 9 for the hooking means 7 and sliding in at least one guide means 19 fixed to said rigid support 9.

In the embodiments of FIGS. 3 and 4, said belt 8 of flexible and elastic material is an endless belt and it slides through at least four guide means 9, with at least two being fixed to each rigid support 9, said belt having two portions 20 each running along a respective one of said rigid supports 9, i.e. in a direction that is generally parallel thereto or substantially perpendicular to the extension direction XX', plus two portions 21 interconnecting them, in this case parallel or in a general direction that is substantially parallel to the extension direction XX'.

In another embodiment as shown in FIG. 5, the device of the invention may include at least two flexible elastic means $8_1$ and $8_2$ each constituted by a belt of flexible deformable material, each having at least one portion 20 mounted along at least one of the rigid supports 9 and sliding through at least one guide means 19, one end of each belt $8_1$, $8_2$ being fixed to one of the rigid supports $9_1$ and its other end being fixed to the other rigid support $9_2$, and if the device is polygonal, that amounts to another rigid support to which the end of the next belt is fixed.

In such an embodiment, there need only be two guide means, one on each of the rigid supports and each corresponding to one of the elastic means $8_1$, $8_2$, together with respective pieces 22 for fixing the ends of two of said elastic means $8_1$ and $8_2$, one at the end of its longitudinal portion 21, in this case extending along the direction XX', and the other by the end of its portion 20 that is substantially perpendicular to said extension direction XX'.

Such devices make it possible to have elastic means with different coefficients and/or capacities for elongation, and thus make it possible to pull on boundaries of hair-carrying zones 16 that are not initially parallel, while still obtaining a traction force-that is homogeneous and continuous, even if the area is extended in a manner that is no longer uniformly parallel.

It would also be possible to place a plurality of elastic devices that are superposed or interleaved in one another, or that are placed in parallel planes, thereby slightly increasing the thickness of the device, thus making it possible to obtain a reserve of elastic energy and traction force that is greater than can be obtained with a single belt line, as shown in FIGS. 3 to 5.

Said guide means 19 may be of any type, such as pulleys mounted free to rotate on axes 11 fixed near an end of each rigid support 9.

Said elastic belt(s) 8, whether in the form of a continuous endless loop as in FIGS. 3 and 4 or in the form of two portions as in FIG. 5 is/are made of a silicone type elastomer material.

In the rest position, as shown in FIG. 4, said rigid supports 9 are practically touching, with the portions 20 perpendicular to the elongation direction XX' having taken up all of the extension of the elastic means 8, said extension having made it possible to establish the longitudinal portions 21 and move the rigid supports 9 apart together with the hooking systems 7, and also subsequently to transmit the force for moving them together via said elastic means 8.

The same applies to the device shown in FIG. 6, where the portions $20_1$ situated along the rigid supports $9_1$ are likewise perpendicular or substantially perpendicular to the extension direction $XX'_1$ of the corresponding rigid support $9_1$; however, the "longitudinal" portions $21_1$ are now no longer parallel to said directions, but form angles that depend on the geometrical shape of the extension polygon that has been imparted to the device.

In the rest position, the device is in the form of a polygon such as a triangle if it has three rigid supports 9, or a pentagon if it has five supports, as shown in FIG. 6, and contact can only be made between the ends of adjacent supports.

To obtain a maximum reserve of energy and elongation, said portions 20 mounted along said rigid supports 9, or perpendicularly to the extension directions XX' thereof, are of the same length l as the corresponding support 9, or they may even be doubled up.

We claim:

1. An implantable device for permanently stretching a selected area of skin tissue, said skin tissue having an underneath side formed of a galea, hypoderma and subcutaneous regions, said skin tissue having an outer surface, the device comprising:

at least two respective hooking systems for securement to the skin tissue to be stretched, the hooking systems disposed in an opposing relationship to each other, each system comprising a generally geometrically configured hooking support and having a common elastic means interconnecting both of said hooking systems, said elastic means having a biased and an unbiased condition, wherein when said elastic means is in said biased condition, each of said hooking systems are positioned in a spaced relationship from each other such that said elastic means operably displaces said hooking supports towards the other so as to place said skin tissue to be stretched under a continuous tensile stretching force, and wherein when said elastic means is in said unbiased condition, said hooking supports are adjacent to each other, said hooking supports each having a side that faces the other, which said sides include a pair of laterally displaced guide means attached thereto for directing said elastic means substantially parallel to and along an extent of said one side, each of said guide means encircling said elastic means so as to prevent pull-out of said elastic means therefrom, said elastic means being exposed between each of said guide means, said hooking supports each having an other, opposing side to said one side, which said other side includes means for hooking said hooking systems to said galea and hypoderm regions of said skin tissue to be stretched.

2. The device according to claim 1, wherein said elastic means is an endless belt sliding through said guide means, said belt having two portions, a first portion disposed along said one side of said hooking support and a second portion interconnecting said hooking supports.

3. The device according to claim 1, including at least two elastic means, each means comprised of a respective belt of a deformable, flexible material, each belt respectively having at least one portion mounted along said one side of the hooking support and sliding through at least one guide means on said respective hooking support, a one end of each belt being fixed to a respective hooking support and an other end being fixed to the opposing hooking support.

4. The device according to claim 1, wherein said elastic means is made of a silicone elastomer material.

5. The device according to claim 1, wherein said guide means are composed of a pair of laterally displaced pulleys mounted to rotate freely, each being mounted on said one side of said hooking support.

6. The device according to claim 1, wherein the respective portions of said elastic means which are disposed parallel to said hooking supports, are of a same length as the corresponding support.

7. The device according to claim 1, further including a slide plate having an area defined by a pair of distal ends and interconnecting sides, said slide plate implanted under said skin tissue so as to rest upon said subcutaneous region of said skin tissue to be stretched, the slide plate having said hooking supports resting thereon and having an area at least an equivalent to an area of said device when said elastic means is in said distended condition.

8. The device according to claim 1, wherein said hooking system includes at least three hooking supports physically positioned to form a polygon configuration having multiple sides, said configuration having as many sides in a rest position as there are hooking supports, said device having twice as many sides in an extended active position as in the rest position.

9. The device according to claim 8, wherein said guide means on each respective hooking support touches an adjacent guide means when said hooking system is in a resting position.

* * * * *